(12) United States Patent
Eudes et al.

(10) Patent No.: US 8,680,366 B2
(45) Date of Patent: Mar. 25, 2014

(54) NANOCARRIER BASED PLANT TRANSFECTION AND TRANSDUCTION

(75) Inventors: Francois Eudes, Lethbridge (CA); Archana Chugh, Lethbridge (CA)

(73) Assignee: Agriculture and Agri-Food Canada (CA)

( * ) Notice: Subject to any disclaimer, the term of this patent is extended or adjusted under 35 U.S.C. 154(b) by 670 days.

(21) Appl. No.: 12/663,458

(22) PCT Filed: Jun. 9, 2008

(86) PCT No.: PCT/CA2008/001112
§ 371 (c)(1),
(2), (4) Date: May 20, 2010

(87) PCT Pub. No.: WO2008/148223
PCT Pub. Date: Dec. 11, 2008

(65) Prior Publication Data
US 2011/0035836 A1   Feb. 10, 2011

Related U.S. Application Data

(60) Provisional application No. 60/929,006, filed on Jun. 7, 2007.

(51) Int. Cl.
*C07K 14/415* (2006.01)
*A61K 31/715* (2006.01)
*A61K 38/00* (2006.01)

(52) U.S. Cl.
USPC ........... 800/278; 800/293; 435/468; 435/470; 514/1.2

(58) Field of Classification Search
None
See application file for complete search history.

(56) References Cited

U.S. PATENT DOCUMENTS

| 2004/0121325 A1 | 6/2004 | Glossl et al. |
| 2005/0260756 A1 | 11/2005 | Troy et al. |
| 2006/0211647 A1* | 9/2006 | Khan .............................. 514/44 |

FOREIGN PATENT DOCUMENTS

| EP | 001 609 | 6/2001 |
| KR | 10-2004-0053645 | 6/2004 |
| WO | 2005-007860 | 1/2005 |
| WO | 2005/117992 A2 | 12/2005 |

OTHER PUBLICATIONS

Jähne et al., Plant Science 109 (1995) 1-12.*
Lindsey et al., Methods in Molecular Biology, 1988, vol. 4, 519-536, Chapter 4, Direct Gene Transfer into Plant Protoplasts.*
Rudolph et al. (The Journal of Biological Chemistry, vol. 278, No. 13, Issue of Mar. 28, pp. 11411-11418, 2003).*
Eudes, Francois et al., "Cell-Penetrating Peptides: From Mammalian to Plant Cells", Plant Signaling & Behavior, Aug. 2008, LNKD-PubMed: 19704463, vol. 3, No. 8, pp. 549-550, XP009135255, ISSN: 1559-2324.
Chen, C. P., et al., "Transfection and expression of plasmid DNA in plant cells by an arginine-rich intracellular delivery peptide without protoplast preparation." FEB Letters, May 1, 2007, Electronic publication Apr. 9, 2007, vol. 581(9), pp. 1891-1897, ISSN: 0014-5793.
Unnamalai, N., et al., "Cationic oligopeptide-mediated delivery of dsRNA for post-transcriptional gene silencing in plant cell." FEBS Letters, May 21, 2004, vol. 566(1-3), pp. 307-310, ISSN: 0014-5793.
Chang, M., et al., "Cellular internalization of fluorescent proteins via arginine-rich intracellular delivery peptide in plant cells." Plant and Cell Physiology, Mar. 2005, vol. 46(3), pp. 482-488, ISSN: 0032-0781, eISSN: 1471-9053.
Rosenbluh, J., et al., "Non-endocytic penetration of core histones into petunia protoplasts and cultured cells: a novel mechanism for the introduction of macromolecules into plant cells." Biochimica et Biophysica Acta, Aug. 30, 2004, vol. 1664(2), pp. 230-240, ISSN: 0006-3002.
Chugh, A., et al., "Translocation and nuclear accumulation of momomer and dimer of HIV-1 Tat basic domain in triticale mesophyll protoplasts." Biochimica et Biophysica Acta, Mar. 2007, Electronic publication Nov. 30, 2006, vol. 1768(3), pp. 419-426, ISSN: 0006-3002.
Mäe, M., et al., "Internalization of cell-penetrating peptides into tobacco protoplasts." Biochimica et Biophysica Acta, May 20, 2005, Electronic publication Jan. 27, 2005, vol. 1669(2), pp. 101-107, ISSN: 0006-3002.
Mahalakshmi, A., et al., "Exogenous DNA uptake via cellular permeabilization and expression of foreign gene in wheat zygotic embryos." Plant Biotechnology, 2000, vol. 17(3), pp. 235-240, ISSN: 1342-4580.
Chugh, A., et al., "Cellular uptakeof cell penetrating peptides and their cargoes in permeabilized wheat immature embryos." The FEBS Journal, May 2008, Electronic Publication Apr. 7, 2008, vol. 275(10), pp. 2403-2414, ISSN: 1742-464X.
Chugh, A., et al., "Cellular uptake of cell-penetrating peptides pVEC and transportan in plants." Journal of Peptide Science, Apr. 2008, vol. 14(4), pp. 477-481, ISSN: 1075-2617.
Chang, M., et al., "Noncovalent protein transduction in plant cells by macropinocytosis." The New Phytologist, 2007, Electronic publication Jan. 5, 2007, vol. 174(1), pp. 45-56, ISSN: 0028-646X, eISSN: 1469-8137.
Cynthia Crane et al., "Transgenic *Medicago truncatula* Plants Obtained From *Agrobacterium tumefaciens*—Transformed Roots and *Agrobacterium rhizogenes*—Transformed Hairy Roots", Plant Biology Division, The Samuel Roberts Noble Founcation, Jan. 9, 2006, pp. 1344-1354.

* cited by examiner

*Primary Examiner* — David T Fox
*Assistant Examiner* — Jared Shapiro
(74) *Attorney, Agent, or Firm* — Harness, Dickey & Pierce, P.L.C.

(57) ABSTRACT

The present invention provides a novel method for the transduction and/or transfection of plant cells. Cell-penetrating peptides (CPPs) have been successfully employed as nanocarriers to deliver proteins and oligonucleotides to single plant cell microspores as well as multi-cellular zygotic embryos. The efficiency of CPP internalization and further delivery of a macromolecular cargo comprising a protein and/or an oligonucleotide can be enhanced by permeabilization of the zygotic embryos.

5 Claims, 12 Drawing Sheets

Continuation of Fig. 1
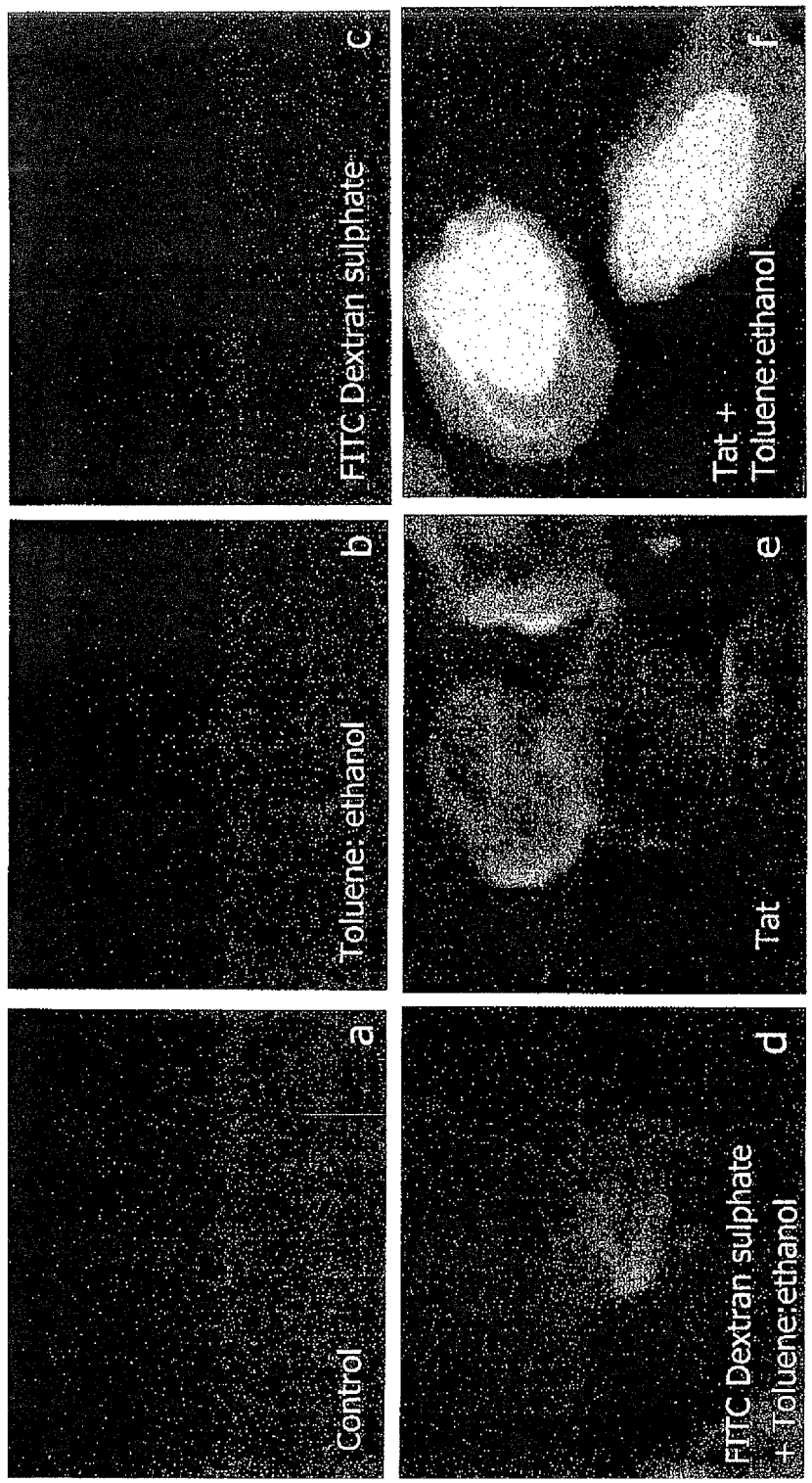

Permeabilized Immaure embryos treated with Tat and GUS enzyme complex. (Protein transduction)

Permeabilized Immature embryos treated with Tat 2a..d GUS enzyme complex. (Protein transduction)

Chariot (Pep-1) + GUS enzyme complex in Permeabilized immature embryos (protein transduction)

Microspores treated with Chariot (pep-1) and GUS enzyme (protein transduction)

*gus* gene expression in permeabilized immature embryos treated with CPP: DNA complexTat+ GUS gene carrying plasmid pAct GUS (transfection)

Plants from microspores treated with Tat/Tat2:DNA complex carrying herbicide resistance gene (transfection)

Fig. 11

Comparison of the visual florescence observed upon translocation of different CPPs in the zygotic embryos in the absence or presence of cellular permeabilizing agent (Toluene: Ethanol)

| | Treatment | Visual fluorescence observed in zygotic embryos | |
|---|---|---|---|
| | | Immature | Mature |
| 1. | Control (-Toluene/Ethanol, -Dexatrn, -Tat) | - | - |
| 2. | Control (Toluene/Ethanol only) | - | - |
| 3. | Control (Dextran Sulphate only) | + | - |
| 4. | pVEC only | + | + |
| 5. | Transportan only | ++ | + |
| 6. | TAT-PTD only | ++ | + |
| 7. | Toluene/Ethanol with Dextran sulphate | ++ | + |
| 8. | Toluene/Ethanol with pVEC | +++ | ++ |
| 9. | Toluene/Ethanol with Transportan | +++ | +++ |
| 10. | Toluene/Ethanol with TAT-PTD | +++++ | ++++ |

NANOCARRIER BASED PLANT TRANSFECTION AND TRANSDUCTION

CROSS-REFERENCE TO RELATED APPLICATIONS

This application is a National Stage of International Application No. PCT/CA2008/001112, filed Jun. 9, 2008. This application claims the benefit of U.S. Provisional Application No. 60/929,006, filed Jun. 7, 2007. The entire disclosures of each of the above applications are incorporated herein by reference.

FIELD

The present invention relates to novel methods and compositions for transformation of plants using cell-penetrating peptides.

BACKGROUND

This section provides background information related to the present disclosure which is not necessarily prior art.

Traditional plant breeding strategies to develop new lines of plants that exhibit particular traits are time consuming and sometimes unpredictable. More recently, the development of methods for plant genetic transformation and the growing identification and availability of useful genes and their products has opened the door to rapid development of plants expressing desired traits. However, there remains a need for improved methods. Existing strategies, such as *Agrobacterum*—mediated transformation and particle bombardment depend heavily on the tissue and genotype. Cell penetrating peptides (CPPs) are a novel and fast growing class of short peptides that are known to play an important role in translocation of a wide range of cargo complexes including proteins and DNA across the bio-membranes in mammalian and human cell lines (Schwartz and Zhang, 2000; Langel, 2002; Vives, 2002,).

The HIV-1 TAT protein transduction domain (PTD) is one of the most well studied translocating peptides. Recent reports have shown the potential of TAT-PTD and its oligomers for plasmid delivery by forming a complex with the negatively charged DNA in mammalian cells (Ignatovich et al, 2003; Rudolph e al, 2003; Siprashvili et al, 2003; Hellgren et al, 2004). Other peptides that have been shown to have translocating properties include pVEC, transportan, penetratin, pep-1 peptides and fragments thereof.

Some of the prior art relating to CPP mediated translocation is discussed below. United States Patent Application 20040121325 describes a method of producing recombinant plants or plant cells which express a sequence coding for a protein having xylosyltransferase activity or being complementary thereto.

PCT Application WO2005117992 discloses a composition for controlled delivery of a compound into a target cell. The composition comprises a cell-penetrating peptide, a cell penetrating peptide inhibitor, a compound, and a cleavage site where the peptide inhibitor inhibits translocation activity of the cell penetrating peptide. Cleavage at the cleavage site by a cleaving agent disinhibits the cell penetrating peptide and the disinhibited cell penetrating peptide is capable of translocating a compound into a target cell. This application does not, however, disclose transformation of plant cells.

United States Patent Application No. 2005/0260756 discloses a membrane permeable complex for facilitating delivery of a double-stranded RNA molecule into a cell. The complex comprises a double-stranded RNA molecule and a cell-penetrating peptide with a covalent bond linking the double-stranded RNA to the cell penetrating peptide. The disclosure is limited to the transformation of neuronal cells.

Unnamalai et al. (FEBS Letters 566 (2004) 307) disclose the use of a cationic oligopeptide polyarginine for delivery of dsRNA for post-transcriptional gene silencing.

While CPPs have been shown to facilitate cargo delivery in mammalian cells, the use of CPP in plant cells for transfection studies has been limited by a number of factors. A major obstacle to adapting this technology to plants is that, unlike animal cells, plant cells present a dual barrier system (cell wall and plasma membrane) for the internalization of CPPs and their cargos. Therefore, CPPs must overcome these two barriers for efficient translocation.

With the ever-growing information from the plant genome-sequencing projects there is an urgent need for the development of a fast, universal (tissue/genotype independent) method in plants for functional genomic studies of a wide array of genes and for the development of transgenic plants expressing desired traits.

SUMMARY

This section provides background information related to the present disclosure which is not necessarily prior art.

The present invention addresses the need for novel methods for gene and/or protein delivery to plant cells. Cell penetrating peptides are used to deliver the desired cargo to the interior of a plant cell.

In one aspect of the invention there is provided a method for the delivery of a cargo moiety to a plant cell. The method comprises exposing a plant cell to a complex comprising at least one cargo moiety linked to a carrier moiety. The plant cell is preferably a somatic cell or a gametophytic cell.

In one preferred embodiment the carrier moiety is a polypeptide that has cell penetration and nucleic acid binding properties. In a further preferred embodiment, the carrier moiety includes a nuclear localization signal.

The carrier moiety may be selected from the group consisting of HIV tat, pVEC, transportan, penetratin, Pep-1 peptides and fragments thereof. Other carriers having cell penetrating properties may also be used in the methods of the invention. In a preferred embodiment, the carrier moiety comprises the protein transduction domain (PTD) of tat or a fragment thereof, preferably amino acids 49 to 57 of HIV tat.

In one aspect of the invention the cargo moiety comprises a nucleic acid. The nucleic acid may comprise mRNA, tm RNA, tRNA, rRNA, siRNA, shRNA, PNA, ssRNA, dsRNA, ssDNA, dsDNA, DNA:RNA hybrids; plasmids, artificial chromosomes, gene therapy constructs, cDNA, PCR products, restriction fragments, ribozymes, antisense constructs or combinations thereof. In one preferred embodiment, the nucleic acid is DNA. In another preferred embodiment, the nucleic acid is RNA.

In another aspect of the invention, the cargo moiety is a polypeptide. In one preferred embodiment, the polypeptide encodes a protein that alters the cell metabolism. The protein may be an embryogenesis related protein or active domain thereof. The protein may be a polypeptide associated with homologous recombination or an active domain thereof.

In an alternative aspect of the invention the cargo moiety also includes a combination of additional polypeptide and/or nucleic acid.

In a preferred embodiment of the invention a somatic plant cell is pre-treated with a cell-permeabilizing agent to facilitate internalization of the complex. A preferred permeabilizing agent is toluene.

In addition to the methods of the invention, the invention also provides a complex for mediating transport of an active substance into a plant cell. The complex comprises a cargo moiety linked to a carrier moiety wherein the carrier moiety can drive the complex into a plant cell.

In preferred embodiments, the cargo moiety is a nucleic acid and the carrier moiety includes a nuclear localization signal. In another embodiment, the complex comprises a fusion protein consisting of cargo moiety and the carrier moiety. A marker protein may be included to track internalization of the complex. Various other types of proteins, such as a protein associated with site directed integration or an embryogenic protein or active domain thereof may be included in the complex.

In another preferred embodiment, the method includes the addition of a transfecting agent, such as LIPO-FECTAMINE®.

The invention also provides transgenic plant seeds and isolated plant cells produced using the methods and constructs of the invention.

Further areas of applicability will become apparent from the description provided herein. The description and specific examples in this summary are intended for purposes of illustration only and are not intended to limit the scope of the present disclosure.

DRAWINGS

These and other features of the invention will become more apparent from the following description in which reference is made to the appended drawings wherein:

FIG. 1 shows the effect of permeabilization on translocation of a fluoresceinated complex in accordance with an embodiment of the present invention;

FIG. 2 demonstrates uptake of Tat in microspores;

FIG. 3 demonstrates the efficiency of various CPPs in permeabilized embryos;

Figure 8:
Figure 9:
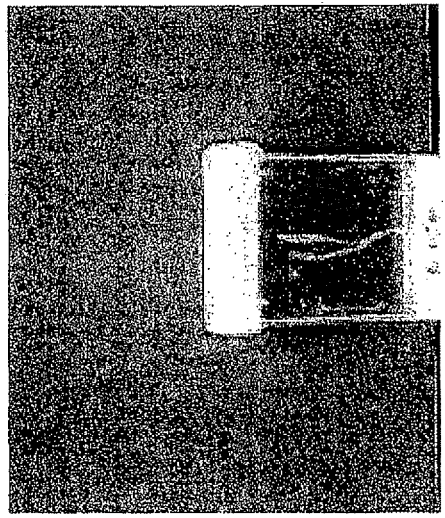
Figure 9:

FIG. 8 demonstrates gus gene expression in permeabilized embryos;

FIG. 9 shows plants from microspores treated with a Tat-DNA complex; and

Figure 10:
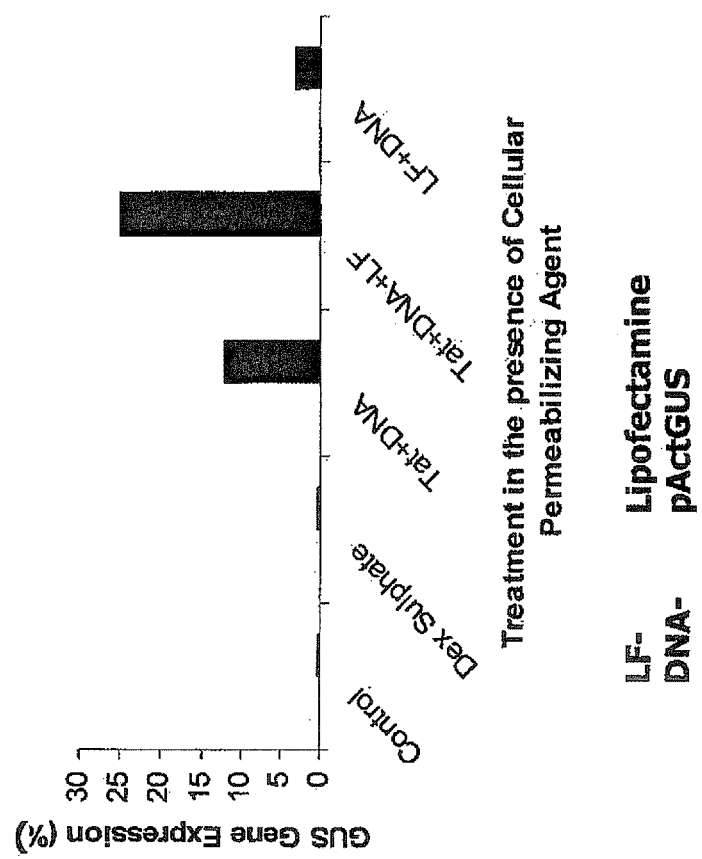

FIG. 10 illustrates the effect of LIPOFECTAMINE® on gus gene expression.

FIG. 11 shows the comparison of the visual florescence observed upon translocation of different CPPs in the zygotic embryos in the absence or presence of cellular permeabilizing agent (Toluene: Ethanol).

Corresponding reference numerals indicate corresponding parts throughout the several views of the drawings.

DETAILED DESCRIPTION

Example embodiments will now be described more fully with reference to the accompanying drawings.

Delivery of foreign nucleic acids or polypeptides across the cell entry barriers of plant cells is difficult. The chances of success can be enhanced by treating the plant tissues with cellular permeabilizing agents such as toluene (Mahalakshmi et al, 2000); however, the rates of transformation remain low.

The present invention provides a novel method for the delivery of a cargo to plant cells. The cargo may be a nucleic acid molecule to be expressed in the target cell or it may be a polypeptide. The cargo may include a marker to track delivery into the plant cells.

In the methods of the present invention, the cargo is linked to a cell-penetrating peptide (CPP), also referred to herein as a "carrier" or "carrier moiety". The carrier is complexed with the cargo and carries the cargo into the cell.

Briefly, a complex comprising a carrier moiety and a cargo moiety is prepared. A carrier moiety is an agent that can transverse a plant cell membrane and/or cell wall.

Preferred carriers for use in the present invention are cell penetrating peptides (CPP). CPPs that are useful in the methods and complexes of the invention include, but are not limited to HIV tat, pVEC, transportan, penetratin, Pep-1 and fragments thereof.

The cargo moiety may be a nucleic acid or a polypeptide. Examples of nucleic acids which may be coupled to the carrier include mRNA, tm RNA, tRNA, rRNA, siRNA, shRNA, PNA, ssRNA, dsRNA, ssDNA, dsDNA, DNA:RNA hybrids; plasmids, artificial chromosomes, gene therapy constructs, cDNA, PCR products, restriction fragments, ribozymes, antisense constructs or combinations thereof. In one preferred embodiment, the nucleic acid is DNA. In another preferred embodiment, the nucleic acid is RNA. Examples of polypeptides which may be complexed with the carrier include any protein or polypeptide fragment thereof. For example, the protein may be an agent that modifies the phenotype of the plant or plant cell. It may be a protein that confers resistance to certain pests or herbicides. The polypeptide may also encode a protein that alters cell metabolism, such as an embryogenesis related protein or a protein involved in site-directed integration.

The carrier-cargo complexes of the invention can be formed in various ways by covalent and/or electrostatic linkage. Also, a complex can be made of combination of CPPs and cargoes e.g. DNA coated with RecA complexed with Pep-1.

In a preferred method of the invention, the cells are first treated with a permeabilizing agent. Surprisingly high rates of transfer can be achieved by combining permeabilization techniques with the use of CPPs. The permeabilization treatment results in transient pore formation in the plasma membrane which can aid in translocation of CPP alone or as a carrier-cargo complex by overcoming size restrictions imposed by the cell wall and membrane. However, it should be clearly understood that pretreatment with a permeabilizing agent is not required for all types of plant cells. For example, microspores can be efficiently transformed using carrier-cargo complexes without any pre-permeabilization step.

Various types of permeabilizing agents can be used to enhance translocation of a carrier-cargo complex. A permeabilizing solution comprising toluene and ethanol has been shown to be particularly effective.

The results of several exemplary experiments are shown in the attached Figures to demonstrate the efficacy of the methods and compositions of the invention.

Figure 1:
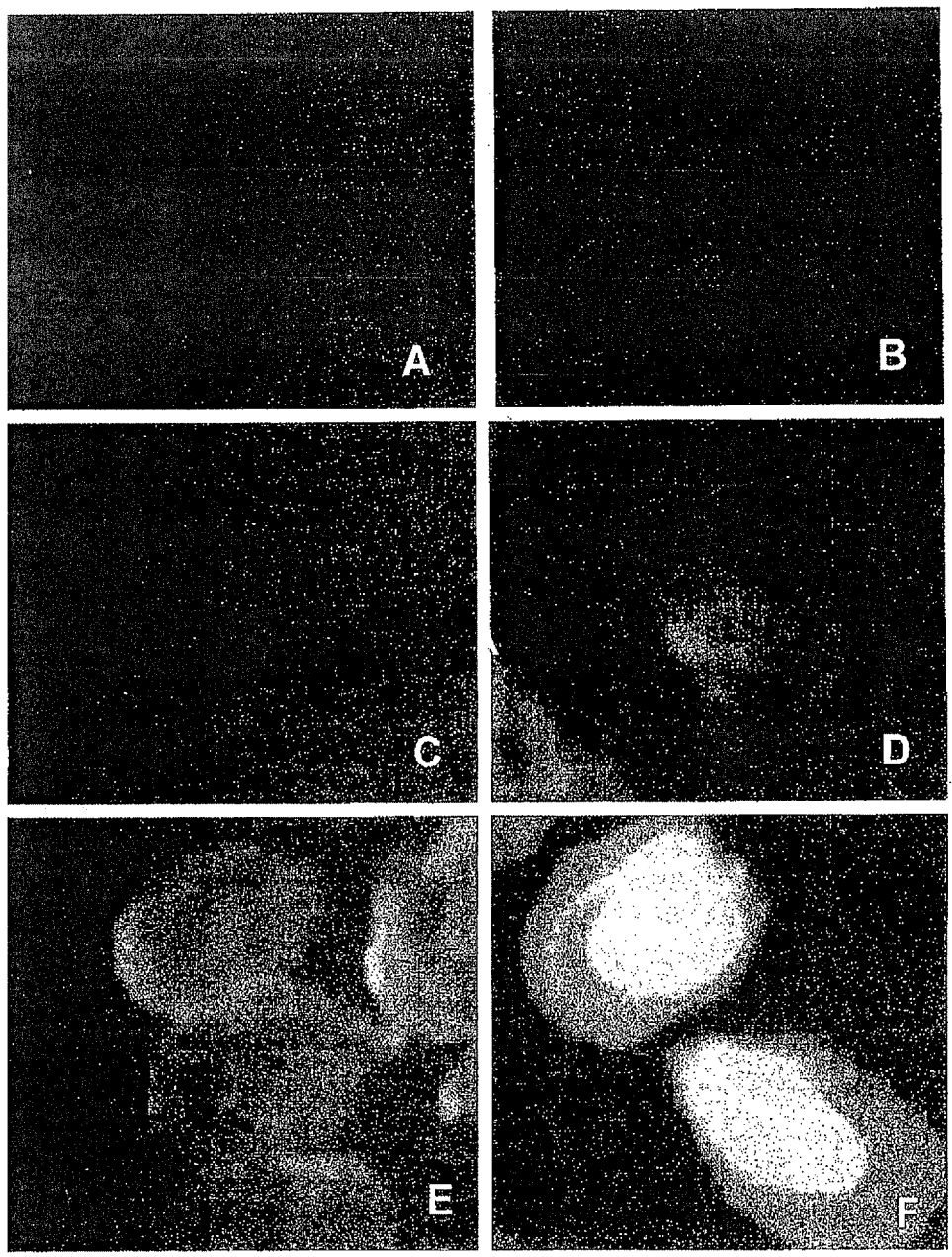

Referring now to FIG. 1, a series of photomicrographs that demonstrate the effect of permeabilization are shown. The translocation of fluoresceinated TAT-PTD in immature embryos of Triticale cv AC Alta was visualized by fluorescence microscopy. The results demonstrate that control embryos incubated in permeabilization buffer only (A) and embryos treated with a Toluene permeabilization buffer (B) did not emit fluorescence. Embryos treated with FITC-labeled dextran sulphate only (C) did not demonstrate any significant uptake of the labeled dextran sulphate. On the other hand embryos treated with FITC-labeled dextran sulphate in the presence of cellular permeabilizing agent (D) did demonstrate some fluorescence as did embryos treated with fluoresceinated TAT-PTD only (E). The most significant uptake, however, was seen in embryos treated with fluoresceinated TAT-PTD in the presence of cellular permeabilizing agent. This demonstrates the high efficiency of transport when cell permeabilization is coupled with the use of a cell penetrating peptide such as TAT-PTD. The results shown in FIG. 1 demonstrate that permeabilization of the immature embryos promotes efficient translocation of cell penetrating peptides.

Figure 2:
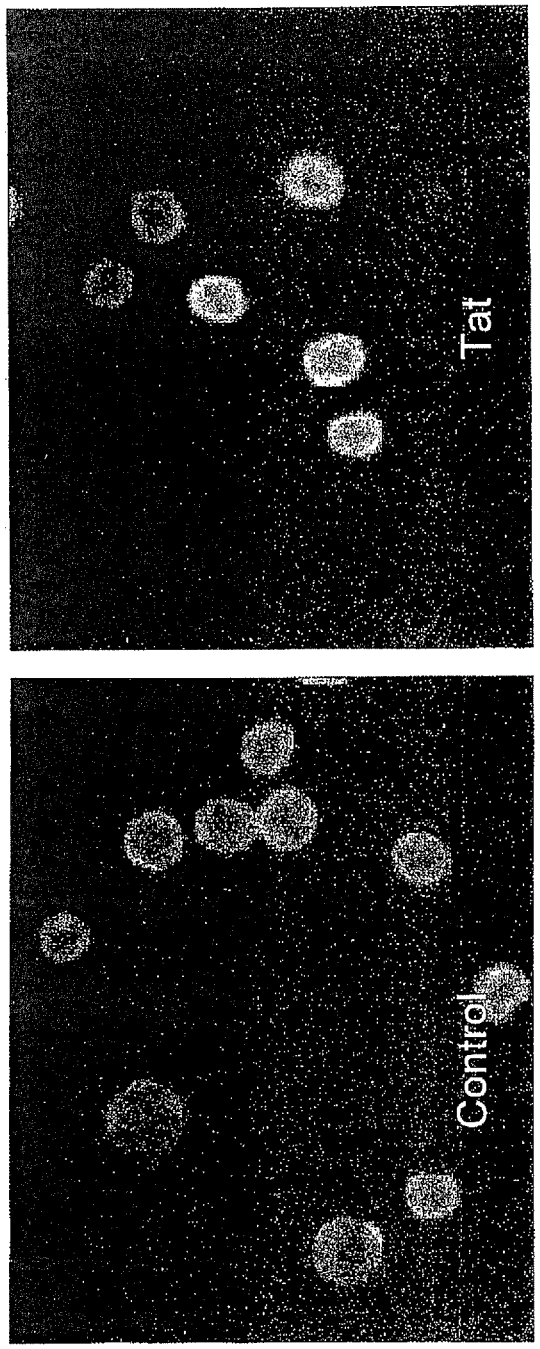

However, permeabilization is not necessary for all cell types. FIG. 2 illustrates the uptake of fluoresceinated Tat by isolated microspores. These results indicate that Tat CPP can penetrate into cells.

Various different types of cell penetrating peptides are useful in the methods of the invention. Table 1 indicates a few of the CPPs investigated.

TABLE 1

| Peptide | Sequence | Peptide Length | Reference |
|---|---|---|---|
| Transportan*[1] | FI-GWTLNSAGYLLGKINLKALAALAKKIL-amide (SEQ ID NO: 1) | 27 | Pooga et al, 2001 |
| pVEC*[2] | FI-LLIILRRRIRKQAHAHSK-amide (SEQ ID NO: 2) | 18 | Elmquist et al, 2003 |
| TAT-PTD*[3] | FI-RKKRRQRRR-amide (SEQ ID NO: 3) | 9 | Futaki et al, 2001 |

For each of these peptides the N-terminal group was fluoresceinated as indicated by "FI". The transportan peptide is a chimeric peptide including 12 amino acids from the neuropeptide galanin in the N-terminus connected with Lys13 to 14 amino acids from the wasp venom mastoparan in the C-terminus. The pVEC peptide was derived from murine vascular endothelial cadherin (amino acid 615-632). The TAT-PTD peptide comprises the HIV-1 TAT protein transduction domain.

TABLE 2

| | | Visual fluorescence observed in zygotic embryos | |
|---|---|---|---|
| | Treatment | Immature | Mature |
| 1. | Control (-Toluene/Ethanol, -Dextrn, -Tat) | − | − |
| 2. | Control (Toluene/Ethanol only) | − | − |
| 3. | Control (Dextran Sulphate only) | + | − |
| 4. | pVEC only | + | + |
| 5. | M-Tat | + | − |
| 6. | Transportan only | ++ | + |
| 7. | TAT-PTD only | ++ | + |
| 8. | Toluene with Dextran sulphate | ++ | + |
| 9. | Toluene with Pvec | +++ | ++ |
| 10. | Toluene + M-Tat | ++ | + |
| 11. | Toluene with Transportan | ++++ | +++ |
| 12. | Toluene with TAT-PTD | +++++ | ++++ |

Table 2 shows the relative fluorescence observed when immature and mature embryos were subjected to various cell-penetrating peptides.

Figure 3:
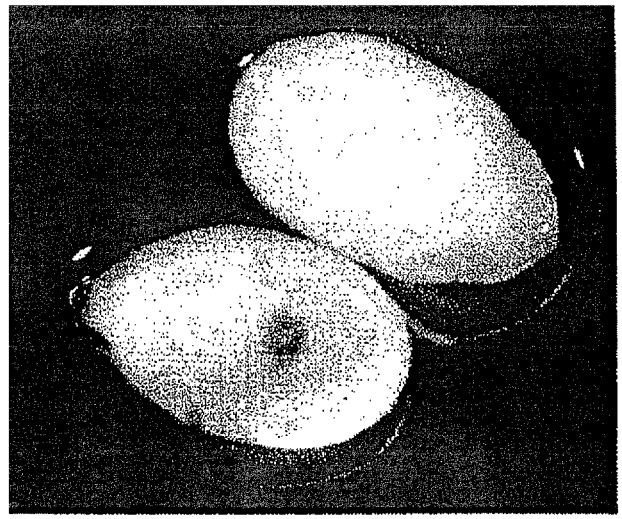

Similar results are presented graphically in FIG. 3. The results indicate that translocation of the various peptides occurs in both mature and immature embryos. The efficiency of translocation is enhanced when the cells are exposed to a permeabilizing agent such as toluene. While toluene has been used as an exemplary agent to illustrate the effect of permeabilization, it is apparent that other permeabilizing agents can be used to achieve the same effect. The results of Table 2 and FIG. 3 using three different CPPs indicates a reasonable prediction that other CPPs would also be useful in the methods of the invention.

The results indicate that the cellular barriers posed by the zygotic embryos can be overcome by permeabilizing the tissue with toluene, resulting in noticeable increase in translocation of all the three peptides investigated. FITC labeled dextran sulphate served as a negative control since it does not possess cell penetration ability. Another negative control, M-tat also showed significantly less fluorescence indicating that the penetration by CPP is highly sequence dependent.

The GUS reporter system (GUS: beta-glucuronidase) is a reporter system that is well known to those skilled in the art of plant molecular biology. This reporter system was used to demonstrate the effects of cell permeabilization and the use of CPPs to enhance the efficiency of protein transduction and gene transfection.

Figure 4:
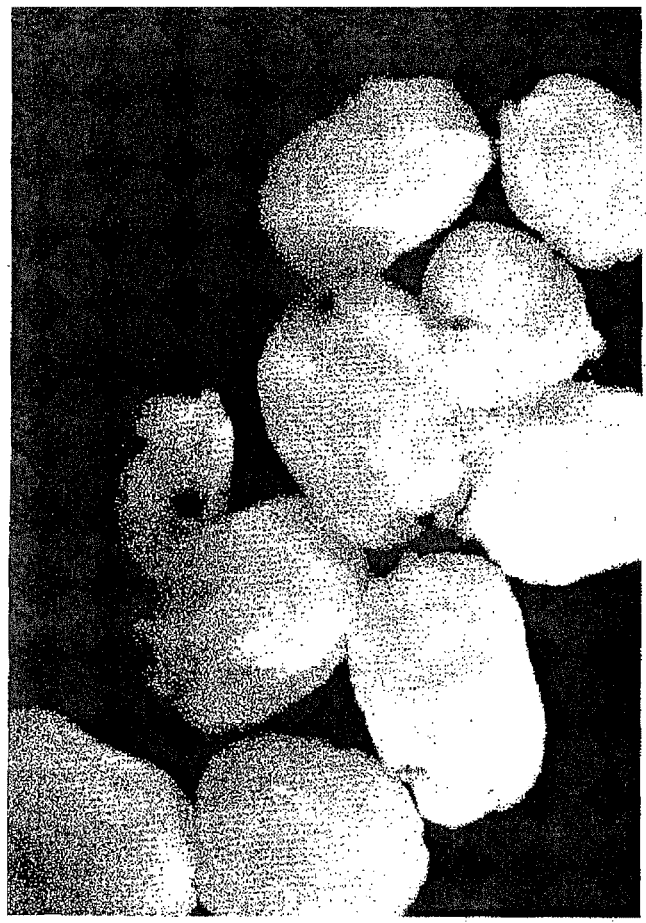
FIG. 4 illustrates uptake of a Tat-GUS complex in permeabilized embryos.
Figure 5:
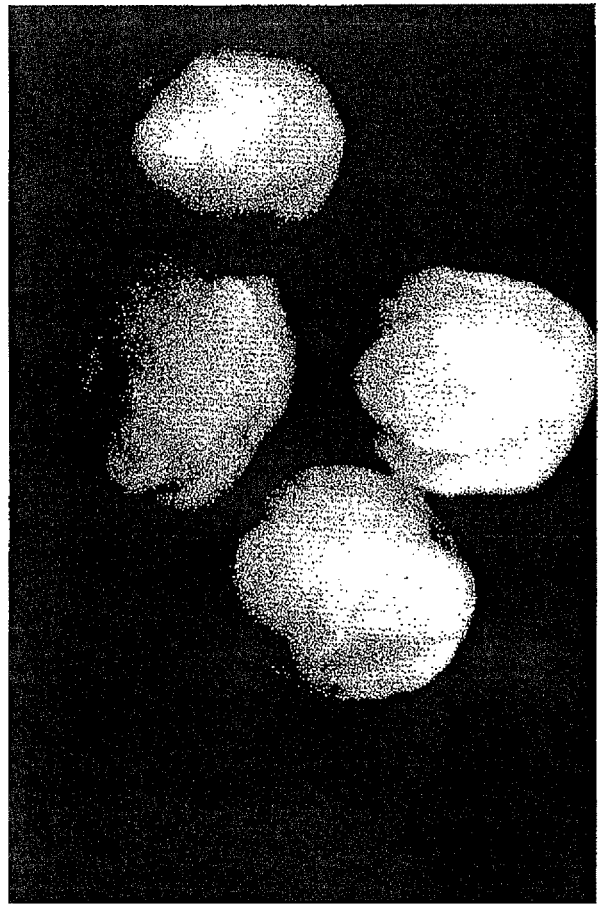
FIG. 5 illustrates uptake of a Tat2-GUS complex in permeabilized embryos.
Figure 6:
FIG. 6 illustrates uptake of a Pep-1-GUS complex in permeabilized embryos.
Figure 6:
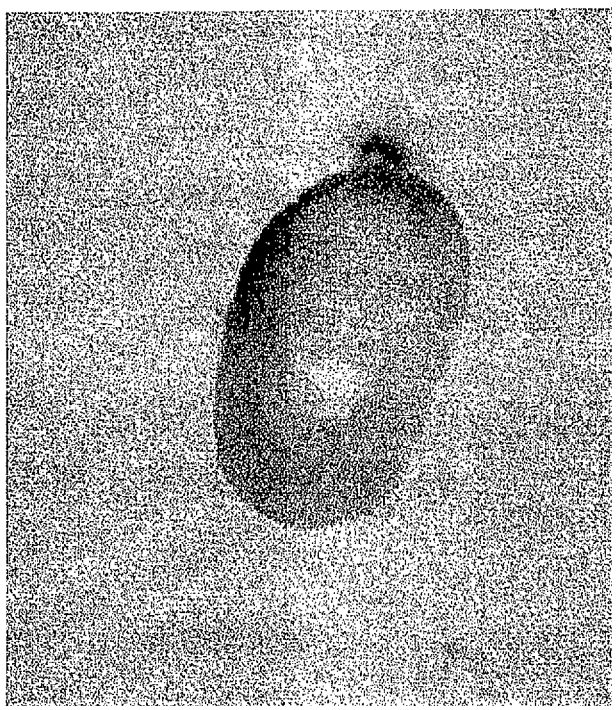
Figure 7:
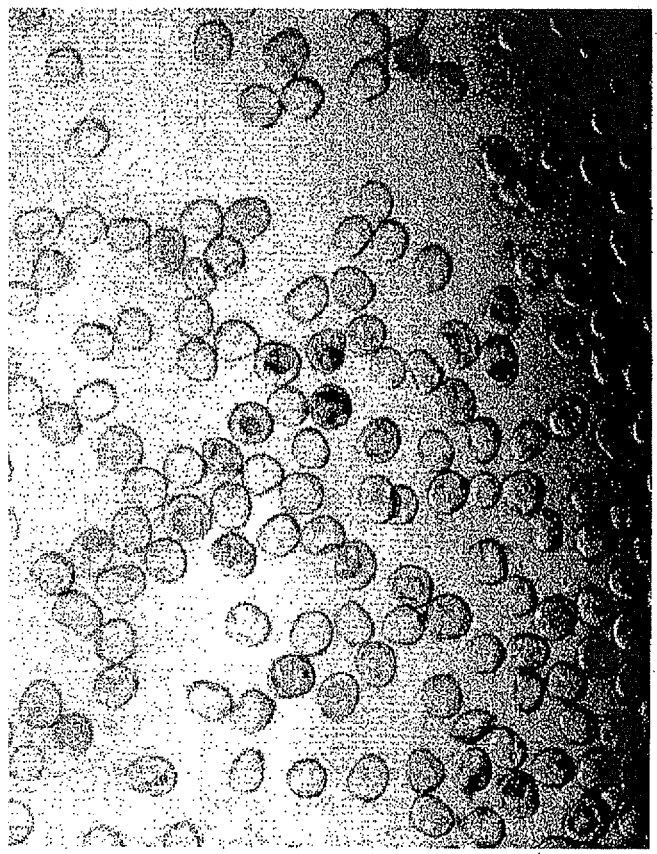
FIG. 7 illustrates uptake of a Pep-1-GUS complex in microspores.

FIG. 4 illustrates the uptake of a Tat-GUS enzyme complex in permeabilized embryos. This photomicrograph clearly demonstrates a highly efficient method of protein transduction. To further enhance uptake, a Tat2 CPP was custom synthesized, Tat 2 is an 18 amino acid dimer of the PTD of HIV Tat. The results using Tat2 as the CPP are shown in FIG. 5. To demonstrate once again that other CPPs can be used in the methods of the invention, a Pep-1-GUS enzyme complex was prepared. The photomicrographs shown in FIG. 6 illustrate that there is efficient protein transduction in permeabilized immature embryos using this complex. FIG. 6A is a control embryo and FIG. 6B demonstrates GUS enzyme delivery mediated by Pep-1. To further demonstrate the efficiency of Pep-1 as a CPP for the delivery of a protein cargo, microspores were treated with the same complex and the results are shown in FIG. 7.

As discussed above, translocation of the CPPs tested was higher in the permeabilized mature and immature embryos. TAT-PTD showed distinct accumulation in the germ area of the immature embryos and the uptake of the TAT-PTD was increased to the highest level (4.7 times) after permeabilization treatment in the immature embryos. Moreover, TAT-PTD is arginine rich with potential to bind the DNA making it a suitable carrier for gene delivery in plant cells/tissues.

In further investigations a TAT-PTD-plasmid DNA complex was assessed for its ability to induce gus gene expression coded by the plasmid in permeabilized embryos. The results are shown in FIG. 8 and clearly indicate that a CPP-plasmid DNA complex can be used to deliver a gene for expression in a plant cell. The GUS transgene expression in the permeabilized embryos was significantly higher than the expression in the non-permeabilized embryos. This strongly suggests that cellular permeabilization plays an important role in translocation of CPP-mediated cargo complex. The results also indicate that complex formation and permeabilization do not compromise the biological activity of the translocated cargo components.

The efficiency of the methods of the invention for gene transfection was further demonstrated using a Tat/Tat2-DNA complex. The DNA carries a herbicide resistance gene. Microspores were transfected and plants were generated. FIG. 9 illustrates that transgenic plants can be generated using the methods of the invention.

The efficiency of plant gene transfection can be further enhanced by including other known transfection promoting agents, such as LIPOFECTAMINE®. When LIPOFECTAMINE® was added to permeabilized cells treated with a CPP-DNA complex the efficiency was increased even more. The results shown in FIG. 10 illustrate that by forming a Tat:DNA complex, transfection rates are higher than when LIPOFECTAMINE® alone is used as a transfecting agent. However, the combination of LIPOFECTAMINE® with the CPP-DNA complex was the most efficient.

While the gus gene and protein reporter system has been used to demonstrate the efficacy of the system, it is clearly apparent that if a large molecule such as GUS can be transported and a complex gene product can be expressed using the methods of the present invention, then other proteins can be transduced and other genes can be transfected.

The methods of the invention have also been used for transduction of embryogenesis related proteins to plant cells. This triggers embryogenesis and can act as a marker. This also provides a novel and universal method of protein delivery to plant cells. Co-delivery of embryogenesis related proteins and a gene of interest provides a novel method for plant genetic engineering.

Variations of the methods described in detail are also encompassed. For example, a peptide with nuclear or other organelle localization domains may be incorporated in the CPP-cargo complexes.

One or more currently preferred embodiments have been described by way of example. It will be apparent to persons skilled in the art that a number of variations and modifications can be made without departing from the scope of the invention as defined in the claims.

The above disclosure generally describes the present invention. It is believed that one of ordinary skill in the art can, using the preceding description, make and use the compositions and practice the methods of the present invention. A more complete understanding can be obtained by reference to the following specific examples. These examples are described solely to illustrate preferred embodiments of the present invention and are not intended to limit the scope of the invention. Changes in form and substitution of equivalents are contemplated as circumstances may suggest or render expedient. Other generic configurations will be apparent to one skilled in the art. Documents such as patents or patent applications referred to herein are hereby incorporated by reference.

EXAMPLES

Although specific terms have been used in these examples, such terms are intended in a descriptive sense and not for purposes of limitation. Methods of microbiology and physics referred to but not explicitly described in the disclosure and these examples are reported in the scientific literature and are well known to those skilled in the art.

Example 1

Plant Cell Preparation

Mature Embryos

The mature embryos (*T. aestivum* cv AC Superb) were isolated and surface sterilized as described by Mahalakshmi et al (2000). The sterilized embryos were air dried in the laminar hood for 1 h prior to use.

Immature Embryos

The embryos were isolated from spikes two weeks post-anthesis (scutellum diameter 1-2 mm). The immature seeds were surface sterilized with 70% ethanol for 30 s followed by treatment with 10% hypochlorite (Chlorex) and a drop of Tween 20, 3 min. Four washings of 1 min each were given with sterile water. The embryos were hand dissected under sterile conditions. Isolated embryos were placed on GEM medium (Eudes et al, 2003) for 24 h in dark at room temperature prior to CPP translocation studies.

Isolated microspores were prepared as described by Amundsen and Eudes, 2005.

Example 2

Translocation of Fluoresceinated Cell Penetrating Peptides in Zygotic Embryos Using Cellular Permeabilizing Agents Peptides were custom synthesized and fluoresceinated at the N-terminal amino group (Alberta Peptide Institute, Canada) (Table 1). FITC-Dextran sulphate (4,000 kDa, Sigma Aldrich) and mutated Tat were used as a negative control.

Isolated and sterilized embryos (20-25) were imbibed in total volume of 420 µl permeabilization buffer (15 mM sodium chloride, 1.5 mM sodium citrate, pH 7.1) containing cellular permeabilization agent toluene/ethanol (1:4) in 1:20 ratio with permeabilization buffer. To this 2.1 µl of 1 mM fluoresceinated CPP was added to give a final concentration of 5 µM. In negative controls, the embryos were treated with FITC-dextran sulphate or M-Tat. The embryos were incubated in the permeabilization mix for 1 h in dark at room temperature, followed by two washings with permeabilization buffer. The embryos were then treated with trypsin:EDTA (0.25% solution, Sigma-Aldrich) in 1:2 ratio with permeabilization buffer for 5 min at room temperature to remove free peptide molecules. Embryos were washed two times with permeabilization buffer and subjected either for fluorescence microscopy or spectrofluorimetric analysis.

Fluorescence Microscopy

Embryos after treatment with cell penetrating peptides and enzymatic degradation of free, extracellular peptides were observed under fluorescence microscope for visual fluorescence (GFP filter; Excitation 470 nm/Emission 525 nm; Leica Inc., Germany).

Translocation of fluoresceinated peptides remarkably increased in the presence of permeabilizing agent (Toluene) in both mature and immature embryos as observed under fluorescence microscope (FIG. 1 and Table 2). The negative controls including treatment with FITC-dextran sulphate and M-Tat showed none or very weak fluorescence (FIG. 1A-D). In general, fluorescence intensity in immature embryos was greater than the mature embryos under both permeabilization and non-permeabilization conditions (Table 2; FIG. 3). Among the three peptides investigated, pVEC showed least uptake even in the embryos treated with cellular permeabilization agent. Interestingly, the permeabilized immature embryos treated with TAT-PTD showed a distinct layer of accumulation in the scutellum and localized accumulation in the germ area of the embryos (FIG. 1F) where as the treatment of permeabilized embryos with other two peptides showed uniform distribution of the fluorescence.

Fluorimetry Analysis

For fluorimetric analysis, the embryos were treated with 500 µl of 1% Triton X-100 (prepared in permeabilization buffer), 30 min, at 4° C. The supernatant was collected in a fresh tube and relative fluorescence uptake by the embryos with different CPPB was estimated by fluorimeter (Biorad, Versafluor, USA Excitation 490/Emission 520).

The fluorimetric analysis also showed remarkable enhancement in the translocation of the cell penetration peptide in the embryos treated with cellular permeabilizing agent, toluene (FIGS. 3A, B). The immature embryos showed higher levels of relative fluorescence uptake for all the peptides in the permeabilized and non-permeabilized immature embryos. In particular, TAT-PTD in immature embryos showed 4.7 times higher relative fluorescence in the permeabilized embryos in comparison to the non-permeabilized embryos. Transportan and pVEC translocation was also increased by 1.8 times and 1.7 times in the permeabilized immature embryos (FIG. 3B). However, the fluorimetric analysis revealed relatively greater translocation of transportan as compared to visual observation for TAT-PTD in the permeabilized and non-permeabilized embryos.

Example 3

CPP-Plasmid DNA Complex Uptake by Permeabilized Immature Embryos

For CPP-DNA complex studies, non-fluoresceinated TAT-PTD was employed for making the complex with DNA (pAct-1GUS). Plasmid DNA and TAT-PTD were mixed together in 1:10 ratio (5 µg DNA: 50 µg TAT-PTD, stocks for both were prepared in optima water) with total volume made up to 100 µl with permeabilization buffer. The mix was incubated at room temperature for 1 h prior to addition to the embryos imbibed in permeabilization buffer. The permeabilizing agent (Toluene) in 1:20 ratio with the buffer was added just before adding the complex to the embryos. The embryos were incubated with the TAT-PTD and DNA complex in the presence of permeabilizing agent for 1 h, followed by two washings with permeabilization buffer. The embryos were plated on GEM containing 250 µg/ml cefotaxime at 25° C. in dark for three days.

GUS Histochemical Assay

The immature embryos were incubated in GUS histochemical buffer (Jefferson, 1987) at 37° C., overnight, with 20% methanol added to avoid any endogenous GUS expression. The percentage GUS expression was calculated as number of treated embryos expressing GUS/total number of treated embryos×100.

The immature embryos incubated with TAT-PTD-plasmid DNA complex in the presence of cellular permeabilizing agent showed transient GUS expression (12%; FIG. 8) whereas the non-treated, negative controls did not show any GUS expression. The embryos treated with TAT-PTD-DNA complex alone without the addition of permeabilizing agent also failed to show any GUS expression signifying the role of permeabilizing agent in facilitating the uptake of TAT-PTD-DNA complex in the immature embryos.

Example 4

CPP Uptake by Various Plant Tissues

Triticale seeds were washed with detergent and grown on moist cotton for one week. The root tip, leaf tip, leaf base and coleoptile were excised and incubated with 5 µM of fluorescently labeled pVEC, scrambled pVEC and transportan. The uptake was maximum in the root tips and leaf bases followed by coleoptile and leaf tip. Transportan showed maximum florescence followed by pVEC, scrambled pVEC and control in which no CPP was added.

Example 5

CPP-Mediated Delivery of GUS Enzyme in Immature Embryos

Triticale immature embryos permeabilized with Toluene, were treated with CPP (Tat or Tat2 or R9)-GUS enzyme complex (4:1 w/w) for one hour in the permeabilization buffer. For Pep-1 the instructions were followed as per the Active Motif for the Chariot kit designed for protein transduction in mammalian cell lines. The CPP-GUS enzyme complex was prepared in the ratio of 4:1 respectively and incubated at the room temperature for one hour. The treated embryos were trypsinized (1:1 trypsin:permeabilization buffer) for five minutes at room temperature resulting in degradation of excess and non-internalized CPP-GUS enzyme complex. After three washes with the permeabilization buffer, the embryos were incubated in the GUS histochemical buffer with 20% methanol (Kosugi et al, 1990) at 37° C. from three hours to overnight for the appearance of blue colour in the treated immature embryos.

Example 6

CPP-Mediated Delivery of GUS Enzyme in Microspores

The Triticale microspores were treated with CPPs (Pep-1, Tat, Tat2, R9) and GUS enzyme complex (4:1) for one hour in NPB-99 medium. The CPP-GUS enzyme complex was prepared as mentioned in examples before. After two washings, trypsinization (1:1 with NPB-99 medium) was performed for five minutes at room temperature. The microspores were incubated in the GUS histochemical buffer with 20% methanol (Kosugi et al, 1990) at 37° C. from three hours to overnight for the appearance of blue colour in the microspores. The positive microspores showed GUS accumulation mainly in their vacuoles.

Example 7

CPP-Mediated Delivery of GUS Enzyme in Onion Epidermal Cells

The ability to deliver functionally active GUS enzyme by CPP R9 was also studied in onion epidermal cells. The complex of R9 and GUS was prepared as mentioned in examples before in the ratio of range of 1-4:1. The onion epidermal cells were incubated with the complex for one hour and thrice with Phosphate buffer Saline pH 7.2. The cells treated with the complex showed appearance of blue colour upon incubation with GUS histochemical buffer for three hours at 37° C. The 4:1 ratio showed maximum blue colour.

Example 8

CPP-Mediated Delivery of Bar Gene in Embryogenic Microspores

The Triticale microspores were treated with complex of CPP (Tat/Tat2) and herbicide (bar) gene coding fragment driven by 'tap' promoter and nos terminator for one-two hours at room temperature. The complex was prepared in 4:1 ratio of tat/tat2 and DNA (w/w), incubation for one hour followed by addition of 5-10 µg of LIPOFECTAMINE 2000® reagent. The cells were washed twice with NPB-99 and further cultured for embryogenesis in NPB-99 medium with 10% Ficoll in the presence of ovaries (Eudes and Amundsen, 2005).

PCR positive calli treated with Tat/tat2 DNA complex+ LIPOFECTAMINE® were obtained as shown in the Table 3 below.

TABLE 3

| Treatment ↓ | Albino Plant | | Green Plant | | Calli | |
|---|---|---|---|---|---|---|
| | Total No | PCR + ve | Total No | PCR + ve | Total No | PCR + ve |
| Control | 6 | 0 | 0 | 0 | 8 | 0 |
| DNA only | 2 | 0 | 0 | 0 | 3 | 0 |
| LF + DNA | 0 | 0 | 0 | 0 | 4 | 0 |
| Tat/Tat$_2$ + DNA | 2 | 0 | 2 | 0 | 0 | 0 |
| Tat/Tat$_2$ + LF + DNA | 6 | 0 | 13 | 0 | 13 | 3 |

Example 9

PHB Genes in Triticale

Triticale tillers for microspore isolation were kept in the refrigerator (4° C.) for 3 weeks with their bases in distilled water and their heads wrapped in aluminum foil. After 3 weeks±3 days, the mid to late uninucleate microspore stage was verified from a median floret using acetocarmine staining prior to extraction. Isolated microspore was carried in Triticale as published in Eudes and Amundsen (2005) for obtaining purified microspore suspension adjusted to 2.5×105 cells per ml of NPB99 medium.

Two transit peptides for chloroplast or mitochondria were cloned in frame with the three genes coding for the enzymes of the PHB metabolic pathways. An equal molar amount of three genetic cassettes with the same transit peptide were used for co-transfection. 1 µg of total DNA diluted in 100 µl sterile water was added to 4 µg of Tat2 diluted in 100 µl, and gently mixed together, resulting in 1:4 ratio of DNA and cell-penetrating peptide (CPP) in the mixture. Following complex incubation for 30 min at RT and 5 µl of LIPOFECTAMINE® was added for 5 min at room temperature, The mixture was added to microspores without supernatant in a 2 ml microcentrifuge tube. Microspores were incubated with the carrier-cargo complex for 15 min and 100 µl of NPB-99 was added and then incubated for 45 min more at RT. The transfected microspores were washed with NPB-99, then centrifuged and the supernatant removed. 1000 µl NPB-99 was added to 2 ml microcentrifuge tube, gently mixed and then 500 ml was pipetted in 35 mm Petri dishes containing 3 ml NPB-99+10% Ficoll (Sigma F4375) (NPB-99-10F) containing Cefotaxime.

Four or five ovaries from similarly sterilized spikes taken directly from the plant were added to each dish containing the microspores. The dishes were sealed with Parafilm and placed in a 150 mm Petri dish around an open 50 mm Petri dish containing sterile distilled water. Then the 150 mm dish was also sealed with Parafilm and incubated in the dark at 28° C. for 20 to 30 days. No selection was applied during the microspore, embryo and plantlet culture.

Regenerated plants were screened by PCR for presence of the three transgenes. RNA was extracted from plants that were PCR positive for the three genes of interest. cDNA was generated from this selection of plants and PCR was performed to confirm expression of the three transgenes Results are shown in the Table 4.

TABLE 4

Co-transfection and simultaneous expression of the three PHB genes

| Organelle transit signal | # transfection experiments | # green plants | # PCR positive for the three genes | # PCR positive on the three cDNAs |
|---|---|---|---|---|
| Chloroplast | 2 | 325 | 38 | 7 |
| Mitochondria | 1 | 21 | 9 | 1 |

Example 10

DNA-Protein Co-Delivery in Triticale Microspores

Triticale tillers for microspore isolation were kept in the refrigerator (4° C.) for 3 weeks with their bases in distilled water and their heads wrapped in aluminum foil. After 3 weeks±3 days, the mid to late uninucleate microspore stage was verified from a median floret using acetocarmine staining prior to extraction. Isolated microspore was carried in Triticale as published in Eudes and Amundsen (2005) for obtaining purified microspore suspension adjusted to 2.5×105 cells per ml of NPB99 medium.

The plasmid (pAct-1 GUS, ~7.2 kb) was linearized with PstI restriction enzyme and DNA was purified by PCR product purification kit (QIAquick, Qiagen, USA). The GUS DNA was delivered following 7 different treatments (T). These experiments were replicated five times.

T1) Control: Control treatment was 200 µl of sterile water.

T2) GUS DNA only: 1 µg of GUS DNA (Sigma Aldrich) diluted in 200 µl of sterile water.

T3) GUS DNA-RecA: 1 µg of DNA diluted in 100 µl sterile water was added to 4 µg of RecA diluted in 100 µl, and gently mixed together, resulting in 1:4 ratio of protein and DNA in the mixture.

T4) DNA-Tat2: 1 µg of DNA diluted in 100 µl sterile water was added to 4 µg of Tat2 diluted in 100 µl, and gently mixed together, resulting in 1:4 ratio of DNA and cell-penetrating peptide (CPP) in the mixture.

T5) DNA-Chariot kit: GUS DNA with the chariot protein transduction kit was transformed by manufacturer's protocol (Active Motif, USA). 1 µg of GUSDNA was diluted into 100 µl sterile water, and 6 µl of chariot was diluted in 100 µl sterile water. The GUS DNA solution was added to the Chariot solution in a 2 ml microcentrifuge tube, for a final volume of 200 µl.

T6) DNA-RecA-Chariot kit: GUS DNA-RecA was delivered in microspores using a Chariot protein transduction kit and the manufacturer's protocol was followed. 4 µg of RecA was diluted 50 µl sterile water and 1 µg of GUS DNA was diluted into 50 µl of sterile water. The RecA solution was added to the DNA solution and incubated for 15 min. 6 µl of chariot was diluted in 100 µl sterile water. The chariot solution was pipetted into the DNA-RecA solution to a final volume of 200 µl in a 2 ml microcentrifuge tube.

T7) DNA-RecA-Tat2: GUS DNA-RecA delivery in microspores by Tat2. 4 µg of RecA was diluted in 50 µl sterile water and 1 µg of GUS DNA was diluted into 50 µl of sterile water. The RecA solution was added to the DNA solution and incubated for 15 min. 4 µg of Tat2 was diluted in 100 µl sterile water. The Tat2 solution was pipetted into the DNA-RecA solution to a final volume of 200 µl in a 2 ml microcentrifuge tube.

Following complex incubation for 15 min at RT and 5 µl of LIPOFECTAMINE® was added for 5 min at RT, The mix was added to only microspores without supernatant in a 2 ml microcentrifuge tube. Microspores were incubated with the carrier-cargo complex for 15 min and 100 µl of NPB-99 was added and further incubated for 45 min more at RT. The transfected microspores were washed with NPB-99, centrifuged and the supernatant removed. 1000 µl NPB-99 was added to a 2 ml microcentrifuge tube and gently mixed. 500 ml was pipetted in 35 mm Petri dishes containing 3 ml NPB-99+10% Ficoll (Sigma F4375) (NPB-99-10F) containing Cefotaxime.

Four or five ovaries from similarly sterilized spikes taken directly from the plant were added to each dish containing the microspores. The dishes were sealed with Parafilm and placed in a 150 mm Petri dish around an open 50 mm Petri dish containing sterile distilled water. The 150 mm dish was also sealed with Parafilm and incubated in the dark at 28° C. for 20 to 30 days.

Embryos larger than 0.5 mm were removed from the Petri dishes and plated onto GEM medium (20 ml in 10 cm Petri dishes; Eudes et al. 2003). The Petri dishes were sealed with Parafilm and placed 30 cm beneath Sylvania Gro-lux wide spectrum bulbs (40 watts) delivering 80 µM m-2 s-1 (16 h light period) with a room temperature at 16° C. Once the embryos turned green, they were aseptically transferred onto 50 ml rooting media in Magenta Vessels, in the same conditions. Once the plant reached the 2-3 leaf stage and had sufficient root growth the plant was transplanted into 4×8 Spencer-Lemaire roottrainer (Spencer-Lemaire Industries Lte., Edmonton) and placed into a growth cabinet with the same conditions as the mother plants. Two weeks after anthesis, ploidy was estimated by checking for seed set.

At 4~5 weeks, embryos were subjected to GUS histochemical assay. The assay was carried out by adding 200 ml of GUS histochemical buffer (500 mM NaH2PO4, 100 mM EDTA, 0.3 M mannitol, 2 mM X-gluc, pH 7.0) to the microspores and then incubating at 37° C., dark, for overnight. The stain solution was removed and the embryos were cleared by PBS. Microspores exhibiting blue colour indicated activity of the exogenously introduced GUS enzyme by CPPs. The percentage of blue embryos in each treatment was calculated using a stereo microscope.

Distinct translocation of Tat2 and Chariot in embryos was observed 2 months after transfection (Table 5). GUS was not observed in negative control; untreated microspores. The highest numbers of embryos that showed GUS upon treatment with Tat2 and Chariot was 25.8 and 26.4%, respectively (Table 5). The second highest frequency of blue embryos was observed with DNA-RecA-Chariot and DNA-RecA-Tat2 treatments. With LIPOFECTAMINE®, DNA and DNA-RecA treatments were able to transfect into microspores at a lower frequency. These studies demonstrate that different DNA and protein complexes were internalized in triticale microspores.

Table 5. Total number of GUS expressed embryos produced by 7 different treatments for gene transformation 2 months after transfection. T1) Control, untreated embryos; T2) DNA; T3) DNA-RecA; T4) DNA-Tat2; T5) DNA-Chariot; T6) DNA-RecA-Chariot; T7) DNA-RecA-Tat2.

TABLE 5

|    | Exp 1 | Exp 2 | Exp 3 | Exp 4 | Exp 5 | Mean ± SD |
|----|-------|-------|-------|-------|-------|-----------|
| T1 | 0     | 1     | 1     | 0     | 1     | 0.6 ± 0.5 |
| T2 | 16    | 16    | 17    | 9     | 17    | 15 ± 3.4  |
| T3 | 21    | 11    | 15    | 17    | 6     | 14 ± 5.7  |
| T4 | 31    | 23    | 29    | 26    | 20    | 25.8 ± 4.4|
| T5 | 32    | 25    | 26    | 27    | 22    | 26.4 ± 3.6|
| T6 | 14    | 16    | 15    | 17    | 23    | 17 ± 3.5  |
| T7 | 18    | 15    | 18    | 12    | 22    | 17 ± 3.7  |

Example 11

DNaseI Protection Assay and Retardation Assay

CPPs-GUS DNA complexes were prepared as described for delivery in example 10 of DNA and CPP complex in triticale microspores DNA (T2) and DNA-RecA (T3). A DNaseI protection assays were performed as described for DNA (T2) and DNA-RecA (T3) delivery of DNA and CPP complex in triticale microspores, but without LIPOFECTAMINE®. Immediately after incubation of peptide-DNA for 20 min, 4 µl of DNaseI (RNase-Free DNase set, Qiagen, USA) was added to the mixture volume (200 µl) and incubated at RT for 15 min followed by 5 min incubation on ice. Peptide-plasmid dissociation and plasmid purification was carried out using a DNA purification kit (QIAquick PCR purification kit).

The DNaseI protection assay showed that DNA, DNA-RecA, DNA-Tat2, DNA-Chariot, DNA-RecA-Chariot, and DNA-RecA-Tat2 with LIPOFECTAMINE® were appreciably protected as the band (7.2 kb) corresponding to DNA was distinctly visible, whereas DNA and DNA-RecA complexes without LIPOFECTAMINE® resulted in degradation of DNA upon treatment with the nuclease (FIG. 11A).

RecA-GUS DNA complexes were prepared as described for delivery of DNA and CPP complex in triticale microspores. 1 µl of GUS DNA was mixed with different concentrations of RecA protein to give ratios of 1:0, 1:4, 1:8, 1:12, 1:16, 1:20 and 1:24. After 20 min incubation without LIPOFECTAMINE®, the 20 µl of complex was subjected to 1% agarose gel.

Gel retardation assays for DNA-RecA complex show that smear fluorescence was observed at 1:8 and higher ratios of and GUS DNA, indicating influence of high concentration of RecA on the reduced mobility of linear plasmid DNA (FIG. 11B). RecA binded to dsDNA at 1:8 and higher ratios.

FIG. 11A shows CPP-DNA complex formations. (A) Different treatments of CPPs and DNA combination were tested for DNaseI protection assay. T1) control, T2) DNA, and T3) DNA-RecA without LIPOFECTAMINE®; T4) DNA, T5) DNA-RecA, T6) DNA-Tat2, T7) DNA-Chariot, T8) DNA-RecA-Chariot, and T9) DNA-RecA-Tat2 with Lipofectamine. FIG. 11B shows the effect of various concentrations of DNA and RecA.

Example 12

Hair Pin Loop Genetic Construct Transfected to Wheat Microspores

TaAOS gene (AY196004) was considered for silencing the jasmonic acid (JA) pathway in wheat using hairpin loop technology. The 27 mer sequence ggccatccgcgaccgcctcgacttcta was chosen as sense strand. The complete gene sequence cloned between the actin promoter and the NOS terminator was (SEQ ID NO: 4)
TCTCGGCCATCCGCGACCGCCTCGACTTCTACTTCCTGTCATAGAAGTC

GAGGCGGTCGCGGATGGCCCT.

1 µg of total DNA diluted in 100 µl sterile water was added to 4 µg of Tat2 diluted in 100 µl, and gently mixed together, resulting in 1:4 ratio of DNA and cell-penetrating peptide (CPP) in the mixture. Following complex incubation for 30 min at RT, 5 µl of LIPOFECTAMINE® was added for 5 min at RT, The mix was added to only microspores without supernatant in a 2 ml microcentrifuge tube.

Microspores from the wheat cultivar, Fielder, were collected as described in previous examples and incubated with the carrier-cargo complex for 15 min. 100 µl of NPB-99 was added and the mix was incubated for 45 min more at RT. Transfected microspores were washed with NPB-99, centrifuged and the supernatant removed. 1000 µl NPB-99 was added to a 2 ml microcentrifuge tube and gently mixed. 500 ml was pipetted into 35 mm Petri dishes containing 3 ml NPB-99+10% Ficoll (Sigma F4375) (NPB-99-10F) containing Cefotaxime. Microspores and embryos were cultured as described in previous examples.

A total of 90 plantlets were produced from the culture from two extractions of microspores. During the first days of acclimatizing to soil, 55 plants died. This unusual high rate of plantlet death once exposed to soil and aerial contaminants was related to the expression of the JA silencing. Regenerated plants (35) were screened by PCR for presence of the transgene. Three of these plants were PCR positive for the transgene.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

SEQUENCE LISTING

<160> NUMBER OF SEQ ID NOS: 4

<210> SEQ ID NO 1
<211> LENGTH: 27
<212> TYPE: PRT
<213> ORGANISM: Artificial Sequence
<220> FEATURE:
<223> OTHER INFORMATION: Chimeric peptide including 12 amino acids from
      the neuropeptide galanin in the N-terminus connected with Lys13 to
      14 amino acids from the wasp venom mastoparan in the C-terminus.
<220> FEATURE:
<221> NAME/KEY: MISC_FEATURE
<222> LOCATION: (1)..(1)
<223> OTHER INFORMATION: N-terminal fluorescein

<400> SEQUENCE: 1

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 2
<211> LENGTH: 18
<212> TYPE: PRT
<213> ORGANISM: Artificial Sequence -continued

```
<220> FEATURE:
<223> OTHER INFORMATION: Derived from murine vascular endothelial
      cadherin (amino acid 615-632).
<220> FEATURE:
<221> NAME/KEY: MISC_FEATURE
<222> LOCATION: (1)..(1)
<223> OTHER INFORMATION: N-terminal fluorescein

<400> SEQUENCE: 2

Leu Leu Ile Ile Leu Arg Arg Arg Ile Arg Lys Gln Ala His Ala His
1               5                   10                  15

Ser Lys

<210> SEQ ID NO 3
<211> LENGTH: 9
<212> TYPE: PRT
<213> ORGANISM: Artificial Sequence
<220> FEATURE:
<223> OTHER INFORMATION: HIV-1 TAT protein transduction domain.
<220> FEATURE:
<221> NAME/KEY: MISC_FEATURE
<222> LOCATION: (1)..(1)
<223> OTHER INFORMATION: N-terminal fluorescein

<400> SEQUENCE: 3

Arg Lys Lys Arg Arg Gln Arg Arg Arg
1               5

<210> SEQ ID NO 4
<211> LENGTH: 70
<212> TYPE: DNA
<213> ORGANISM: Artificial Sequence
<220> FEATURE:
<223> OTHER INFORMATION: Sequence cloned between actin promoter and NOS
      terminator.

<400> SEQUENCE: 4
tctcggccat ccgcgaccgc ctcgacttct acttcctgtc atagaagtcg aggcggtcgc    60
ggatggccct                                                          70
```

What is claimed is:

1. A method for obtaining a genetically engineered plant, said method comprising exposing plant cells haying a cell wall to a carrier-cargo complex comprising at least one polynucleotide cargo moiety linked to a nuclear targeting cell penetrating peptide (CPP) carrier moiety selected from the group consisting of HIV-tat, pVEC, transportan, penetratin, Pep-1 peptides and fragments thereof to obtain transduced cells and propagating the plant cells to form a plant, wherein the plant cells are embryo cells pre-treated with a cell permeabilizing agent comprising toluene or microspores.

2. The method according to claim 1, wherein the microspore is uninucleated or has an open micropore or is both uninucleated and has an open micropore.

3. The method according to claim 1, wherein the carrier moiety is a dimer of amino acid 49-57 of HIV tat.

4. The method according to claim 1, wherein the polynucleotide cargo moiety is selected from the group consisting of ssRNA, dsRNA, ssDNA, dsDNA and DNA:RNA hybrids.

5. The method according to claim 1, comprising treating the cell with the carrier-cargo complex and a transfecting agent.

* * * * *